(12) United States Patent
Kaneda (10) Patent No.: US 10,746,687 B2
(45) Date of Patent: Aug. 18, 2020

(54) METHOD FOR MEASURING TARGET COMPONENT AND APPARATUS FOR MEASURING TARGET COMPONENT

(71) Applicant: ARKRAY, Inc., Kyoto (JP)

(72) Inventor: Hisashi Kaneda, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 470 days.

(21) Appl. No.: 15/366,167

(22) Filed: Dec. 1, 2016

(65) Prior Publication Data

US 2017/0160223 A1    Jun. 8, 2017

(30) Foreign Application Priority Data

Dec. 7, 2015 (JP) ................. 2015-238533
Nov. 29, 2016 (JP) ................. 2016-231201

(51) Int. Cl.
*G01N 27/327* (2006.01)
*C12Q 1/00* (2006.01)

(52) U.S. Cl.
CPC ......... *G01N 27/3274* (2013.01); *C12Q 1/006* (2013.01); *G01N 27/3272* (2013.01)

(58) Field of Classification Search
CPC ...... G01N 27/48; G01N 27/26; G01N 27/327; G01N 27/10; G01N 27/06; G01N 33/49; G01N 33/80; G01N 33/26; A61B 5/05; A61B 5/14532; A61B 5/14535
See application file for complete search history.

(56) References Cited

U.S. PATENT DOCUMENTS

| 8,760,178 B2 | 6/2014 | Rippeth | |
| 2003/0213693 A1* | 11/2003 | Selvaganapathy | ........................ G01N 27/4473 204/452 |
| 2010/0000880 A1 | 1/2010 | Itoh et al. | |
| 2014/0090988 A1* | 4/2014 | Malecha | ............ G01N 27/3272 205/777.5 |
| 2014/0174948 A1* | 6/2014 | Lee | ........................ C12Q 1/001 205/777.5 |

FOREIGN PATENT DOCUMENTS

| EP | 1256798 A1 | 11/2002 |
| EP | 2840389 A1 | 2/2015 |
| GB | 2515299 A | 12/2014 |
| JP | 3102613 B2 | 8/2000 |
| JP | 5239860 B2 | 7/2013 |

OTHER PUBLICATIONS

Extended European Search Report issued in corresponding European Patent Application No. 16202378.2 dated Apr. 12, 2017.
Pandurangachar et al., "Electrochemical Investigations of Potassium Ferricyanide and Dopamine by 1-butyl-4-methylpyridinium tetrafluoro borate Modified Carbon Paste Electrode: A Cyclic Voltammetric Study," International Journal of Electrochemical Science, 5: 1187-1202 (2010).

* cited by examiner

*Primary Examiner* — Gurpreet Kaur
(74) *Attorney, Agent, or Firm* — Morgan, Lewis & Bockius LLP (57) ABSTRACT

The disclosure provides target component measurement methods and target component measurement apparatus for measuring target components including glucose.

16 Claims, 8 Drawing Sheets

METHOD FOR MEASURING TARGET COMPONENT AND APPARATUS FOR MEASURING TARGET COMPONENT

TECHNICAL FIELD

The present invention relates to a method for measuring a target component and an apparatus for measuring a target component.

BACKGROUND ART

Blood glucose concentration may be measured by an electrochemical measurement method that uses glucose oxidase or glucose dehydrogenase, an electron transfer substance, and an electrode, where a voltage equal to or higher than the oxidation potential of the electron transfer substance is applied to the electrode, and the glucose concentration is calculated based on the measured value.

The glucose concentration calculated by the above-described measurement method, however, may contain errors due to interfering substances, such as hematocrit, ascorbic acid, and the like in blood. Therefore, these interfering substances should be measured by using a different electrode compared to an electrode used to measure the glucose, and the amount of glucose should be calibrated based on the measured values (Japanese Patent Nos. 3102613 and 5239860).

Thus, there is a demand for a new method for measuring glucose.

BRIEF SUMMARY OF THE INVENTION

Problem to be Solved by the Invention

The present invention provides a new target component measurement method and a new target component measurement apparatus for measuring target components including glucose, for example.

Means for Solving Problem

The present invention solves existing problems associated with measuring a target component by providing a method for measuring a target component (hereinafter, also referred to as a "measurement method") that includes the following steps: applying a first voltage ($V_1$) to an electrode system in the presence of a sample, a redox catalyst for a target component, and an electron transfer substance; applying a second voltage ($V_2$) to the electrode system; and acquiring a signal from the electrode system during the second voltage application step, wherein the first voltage is a voltage equal to or higher than an oxidation potential (E) of the electron transfer substance, and the second voltage is a voltage lower than the oxidation potential (E) of the electron transfer substance.

The present invention also provides an apparatus for measuring a target component (hereinafter, also referred to as a "measurement apparatus"), including: an electrode system; a voltage application unit that applies a first voltage ($V_1$) and a second voltage ($V_2$) to the electrode system in the presence of a sample, a redox catalyst for a target component, and an electron transfer substance; and a signal acquisition unit that acquires a signal from the electrode system during the second voltage ($V_2$) application, wherein the first voltage is equal to or higher than an oxidation potential (E) of the electron transfer substance, the second voltage is lower than the oxidation potential (E) of the electron transfer substance, and the apparatus is used in the method for measuring a target component according to the present invention.

Effects of the Invention

According to the present invention, target components, including glucose, may be measured.

MODE FOR CARRYING OUT THE INVENTION

In the measurement method and measurement apparatus according to the present invention, for example, the first voltage ($V_1$) is a voltage satisfying $E \leq V_1 \leq E+1.15$. The first voltage ($V_1$) is, for example, higher than an oxidation potential (E) of the electron transfer substance.

In the measurement method and measurement apparatus according to the present invention, for example, the second voltage ($V_2$) is a voltage satisfying $E-0.25 \leq V_2 < E$.

In the measurement method and measurement apparatus according to the present invention, for example, the signal is a signal acquired within 0.4 seconds with reference to the time of the second voltage application.

In the measurement method and measurement apparatus according to the present invention, for example, the signal is a signal acquired at a single time point.

In the measurement method and measurement apparatus according to the present invention, for example, the signal continuously acquired.

In the measurement method and measurement apparatus according to the present invention, for example, the signal includes signals acquired at a plurality of time points.

In the measurement method and measurement apparatus according to the present invention, for example, the target component is glucose.

In the measurement method and measurement apparatus according to the present invention, for example, the redox catalyst is oxidoreductase or dehydrogenase.

In the measurement method and measurement apparatus according to the present invention, for example, the redox catalyst is glucose oxidase or glucose dehydrogenase.

In the measurement method and measurement apparatus according to the present invention, for example, the sample is a biological sample including blood.

The measurement method according to the present invention includes: calculating an amount of a target component in the sample from the signal, for example.

The measurement method according to the present invention includes: acquiring a correction signal by the electrode system; and correcting the signal based on the correction signal, wherein in the calculation step, the amount of the target component in the sample is calculated from a corrected signal, for example.

The measurement apparatus according to the present invention includes a calculation unit that calculates the amount of a target component in the sample from the signal, for example.

The measurement apparatus according to the present invention includes: a correction signal acquisition unit that acquires a correction signal by the electrode system; and a correction unit that corrects the signal based on the correction signal, wherein the amount of the target component in the sample is calculated from a corrected signal by the calculation unit, for example.

<Method for Measuring a Target Component>

As described above, the method for measuring a target component according to the present invention is a method including the following steps: applying a first voltage ($V_1$) to an electrode system in the presence of a sample, a redox catalyst to a target component, and an electron transfer substance; applying a second voltage ($V_2$) to the electrode system; and acquiring a signal by the electrode system in the second voltage application step, wherein the first voltage is equal to or higher than the oxidation potential (E) of the electron transfer substance, and the second voltage is lower than the oxidation potential (E) of the electron transfer substance. The measurement method according to the present invention is characterized in that the first voltage is equal to or higher than the oxidation potential of the electron transfer substance and the second voltage is lower than the oxidation potential of the electron transfer substance, and other steps and conditions are not limited.

In one aspect, after the application of the first voltage equal to or higher than the oxidation potential of the electron transfer substance, the signal acquired at the time of applying the second voltage lower than the oxidation potential of the electron transfer substance changes in response to the amount of the target component in the sample. Specifically, for example, after the application of the first voltage, the transient current obtained after the start of the application of the second voltage shows the negative correlation with the amount of the target component in the sample and arrived at the present invention. The measurement method according to some embodiments of the present invention reduces the influence of the interfering substances such as hematocrit, ascorbic acid, and the like in the measurement of the target component, for example. Therefore, the measurement method according to the present invention can be carried out even by a biosensor having a simple structure that does not include an electrode for measuring the interfering substances, for example. Furthermore, for example, the measurement method according to the present invention may be carried out without acquiring a correction signal for correcting the influence of the interfering substance because the influence of the interfering substance is reduced. Thereby, for example, according to the measurement method of the present invention, the number of acquisitions of signal may be reduced, and the influence of measurement error generated in acquisition of signal may be reduced. This allows a target component to be measured with a high degree of reproducibility. According to Japanese Patent Nos. 3102613 and 5239860, a signal may be acquired in a state where a Cottrell current is stable after the application of a voltage to the electrode system. On the other hand, the measurement method according to the present invention may be carried out before the Cottrell current becomes stable, for example. Thus, according to the measurement method of the present invention, for example, the time required for measurement may be reduced. In addition, for example, the measurement method according to the present invention may be carried out by a biosensor that includes an electrode system for use in a known electrochemical measurement method by adjusting the voltage applied to the electrode system and the signal acquisition time. Therefore, for example, the measurement method of the present invention may be applied to a known biosensor inexpensively.

In the present invention, for example, "to acquire a signal" can also be referred to as "to measure a signal" and "to acquire or measure a "signal"" means "to acquire or measure a "signal value" showing the size, strength or the like of the signal". The change of the signal means the change of the signal value, for example.

In the present invention, the "oxidation potential" is, for example, the potential of the electrode system in an oxidation reaction system including the electron transfer substance and the electrode system. The oxidation potential may be measured by the measurement under the following oxidation potential measurement condition using: a measurement system of the oxidation potential that includes the electron transfer substance; and an electrode system that includes a working electrode, a counter electrode, and a reference electrode or an electrode system that includes the working electrode and the reference electrode, in the state where the counter electrode or the working electrode is connected to the reference electrode, for example. On this occasion, a potential that shows a forward peak current value in the obtained current value is the oxidation potential. The oxidation potential may be determined based on the potential obtained by a single measurement or based on the potentials obtained by multiple measurements, for example. In the latter case, the oxidation potential may be the average potential, the minimum potential, or the maximum potential of the potentials obtained by multiple measurements or may be in the range from the minimum potential to the maximum potential of the potentials obtained by multiple measurements, for example. The oxidation potential may be a preliminarily measured oxidation potential or an oxidation potential measured at the time of measuring the target component, for example. As a specific example, in the case where the electron transfer substance is a ruthenium complex and the material for the electrode system is carbon, the oxidation potential is, for example, from 30 to 50 mV. In some embodiments, the oxidation potential of the electron transfer substance may be from about 10, 20, 30 or 40 mV to about 40, 50, 60 or 70 mV.

(Oxidation Potential Measurement Condition)

Concentration of electron transfer substance in measurement system: 10 to 500 mmol/L Sample used in measurement system: blood specimen Temperature of measurement system: 25° C.
Initial potential: −800 mV
Switching potential: 800 mV
Sweep rate: 20 mV/s The measurement method according to the present invention may be a qualitative analysis of measuring the presence or absence of the target component in the sample or a quantitative analysis of measuring the amount of the target component in the sample, for example.

In the present invention, the first voltage application step, the second voltage application step, and the signal acquisition step are performed in the presence of the sample, the redox catalyst, and the electron transfer substance. In other words, for example, the measurement method according to the present invention applies the first voltage application step, the second voltage application step, and the signal acquisition step to a reaction system including the sample, the redox catalyst, and the electron transfer substance. The reaction system is, for example, preferably a liquid system. The reaction system may be a redox solution or a reaction solution that includes the sample, the redox catalyst, and the electron transfer substance.

In the present invention, the sample is not limited to a particular sample and may be, for example, a liquid sample. Examples of the liquid sample include living body-derived specimens (biological samples), and the liquid sample can be a diluted solution, a suspension, or the like of the biological sample. Examples of the biological sample include body fluids such as blood, urine, gastric juice, expectoration, an amniotic fluid, a peritoneal fluid, an interstitial fluid, and the like; tissues such as the large intestine, the lung, and the like; and cells such as oral cells, germ cells, cells derived from nail and hair, and the like. Examples of the blood include whole blood, blood plasma, blood serum, and hemolysate. The sample may be a sample that includes the target component or a sample that may or may not include the target component, for example.

In the present invention, the target component is not limited to a particular component, and examples thereof include sugar, such as glucose, C-reactive protein (CRP), HbA1c, thyroid-stimulating hormone (TSH), FT3, FT4, hCG, HBs antigen, HBc antibody, HCV antibody, TY antigen, anti-streptolysin O (ASO), type IV collagen, matrix metalloproteinase-3 (MMP-3), PIVAK-II, α1 microglobulin, β1 microglobulin, amyloid A (SAA), elastase 1, basic fetoprotein (BFP), *Candida* antigen, uterus cervical mucous granulocyte elastase, digoxin, cystatin C, factor XIII, urinary transferrin, syphilis, hyaluronic acid, fibrin monomer complex (SFMC), von Willebrand factor (factor VIII associated antigen), protein S, rheumatoid factor (RF), IgD, α1 acid glycoprotein (α1AG), α1 antitrypsin (α1AT), α2 macroglobulin, albumin (Alb), ceruloplasmin (Cp), haptoglobin (Hp), prealbumin, retinol-binding protein (RBP), β1C/β1A globulin (C3), β1E globulin (C4), IgA, IgG, IgM, β lipoprotein (β-LP), apoprotein A-I, apoprotein A-II, apoprotein B, apoprotein C-II, apoprotein C-III, apoprotein E, transferrin (Tf), urinary albumin, plasminogen (PLG) and lipoprotein (a) (LP(a)), lactic acid, low density lipid, high density lipid, and triglyceride. In the present invention, a target component to be measured may be one type or two or more types, for example.

In the present invention, for example, the redox catalyst is a catalyst that catalyzes the redox reaction of the target component, and the redox catalyst may catalyze either one of or both of an oxidation reaction and a reduction reaction. The redox catalyst is not limited to a particular catalyst and can be determined appropriately according to the target component, for example. Examples of the redox catalyst include oxidase, reductase, oxidoreductase, and dehydrogenase. As a specific example, in the case where the target component is glucose, the oxidase may be, for example, glucose oxidase or the like and the dehydrogenase can be, for example, glucose dehydrogenase or the like. In the case where the target component is a lactic acid, the oxidoreductase can be, for example, lactic acid oxidoreductase or the like and the dehydrogenase can be, for example, lactic acid dehydrogenase or the like. The redox catalyst (for example the oxidoreductase) may further include a cofactor, for example. The cofactor is not limited to a particular cofactor and can be determined appropriately according to the type of the redox catalyst (for example the oxidoreductase), for example. Examples of the cofactor include flavin-adenine dinucleotide (FAD), pyrroloquinoline quinone (PQQ), nicotinamide adenine dinucleotide (NAD), and nicotinamide adenine dinucleotide phosphate (NADP). For example, one type of redox catalyst (for example the oxidoreductase) may be used alone or two or more types of redox catalyst (for example the oxidoreductase) may be used in combination.

In the present invention, for example, the electron transfer substance may be a substance that accepts an electron generated by the redox reaction of the target component and the redox catalyst and donates the electron to the electrode system or the electron transfer substance may be a substance that accepts an electron from the electrode system and donates the electron to the redox reaction of the target component and the redox catalyst. The electron transfer substance is not limited to a particular substance and can be determined appropriately according to the type of the redox catalyst, for example. Specifically, examples of the electron transfer substance include a ruthenium complex, ferricyanide, an osmium complex, an iron complex, other organometallic complexes, an organometallic complex polymer, conductive ionic salt, an organic compound such as benzoquinone or the like, and a conductive redox polymer. For example, one of the electron transfer substances may be used alone or two or more of them may be used in combination.

In the present invention, for example, the electrode system is an electrode that detects a signal generated by the redox reaction of the target component and the redox catalyst. The electrode system is provided with at least one set of electrode group that includes a working electrode which is the detection site of the signal and a counter electrode, for example. The electrode system, for example, may comprise one, two, three, four or more sets of electrode groups. The electrode system, for example, may comprise one, two, three, four or more working electrodes. In the latter case, two, three, four or more working electrodes may be different working electrodes, for example. The different working electrodes may be those made of different materials or those detecting different target components. For example, the redox catalyst and the electron transfer substance may preliminarily be placed on the working electrode, and the working electrode may be coated with the redox catalyst and the electron transfer substance. In this case, for example, the target component may be measured by bringing the electrode system into contact with the sample. Thus, the target component may be measured more easily. In the electrode system, the number of the counter electrodes may be one or two or more, for example. In the electrode system, for example, the electrode groups may include different counter electrodes or the counter electrode of one electrode group may also serve as the counter electrode of another electrode group. The electrode system may include other electrodes such as a reference electrode and the like as needed, for example. The material for each electrode of the electrode system is not limited to a particular material and can be determined appropriately according to the types of the target component, the redox catalyst, and the electron transfer substance, for example.

In some embodiments, the electrode system is also connected to a signal acquisition unit and the signal acquisition unit is connected to the working electrode. In this case, for example, the working electrode may be connected to the signal acquisition unit through a terminal. The signal acquisition unit may be, for example, a detector or the like. The detector is not limited to a particular detector and examples thereof include a current detector, a potential detector, and a voltage detector. The detector may include a current/voltage converter, an A/D converter, a computing unit, or the like, for example.

As the electrode system, for example, an electrode system for a biosensor used in a known electrochemical measurement method that can measure the target component may be used. When the biosensor is used as the electrode system, for example, the biosensor includes the detector and an electrode system provided with at least one set of electrode group that includes the working electrode and the counter electrode, and the detector is connected to the working electrode. In the biosensor, for example, the detector may be placed inside or outside the biosensor. In the latter case, for example, the biosensor may preliminarily be connected to the detector before acquisition of the signal or the biosensor may be connected to the detector at the time of acquisition of the signal.

The biosensor may further include an introducing section that introduces the sample and a transfer section that transfers the sample to the electrode system, for example. The redox catalyst and the electron transfer substance may be placed in the biosensor. For example, the redox catalyst and the electron transfer substance can be placed on the working electrode, the introducing section, or the transfer section. The redox catalyst and the electron transfer substance may be placed on one site or on two or more sites, for example. When the redox catalyst and the electron transfer substance are placed on the working electrode, for example, the working electrode is coated with the redox catalyst and the electron transfer substance. When the biosensor includes two or more working electrodes, the redox catalysts and the electron transfer substances placed on the working electrodes may be the same or different.

In the present invention, the signal is a signal that can be acquired by the electrode system. The signal is not limited to a particular signal and can be a signal based on the redox reaction of the target component and the redox catalyst, for example. In some embodiments, the signal may be an electrical signal. Examples of the electrical signal include a current, a voltage converted from a current, an electrical quantity calculated from a current and time, and digital signals corresponding thereto. These electrical signals can be mutually converted by a known method, for example. In some embodiments, when a current is measured by an electrode system, the current may be converted into a voltage, for example, by the current/voltage converter or the like and a voltage which is an analog signal can be converted into a digital signal, for example, by an A/D (analog/digital) converter.

As described above, in the first voltage application step, the first voltage is applied to the electrode system in the presence of the sample, the redox catalyst to the target component, and the electron transfer substance. The first voltage application step can be performed by bringing the electrode system into contact with the reaction system that includes the sample, the redox catalyst, and the electron transfer substance to apply the first voltage to the electrode system, for example. The reaction system may be prepared by adding the redox catalyst and the electron transfer substance to the sample. When the electrode system of the biosensor is used as the electrode system, for example, the reaction system may be prepared by bringing the sample into contact with the electrode system coated with the redox catalyst and the electron transfer substance. The first voltage can be applied to the electrode system using a voltage application unit, for example. The voltage application unit is not limited to a particular unit as long as a voltage can be applied to the electrode system, for example, and a voltage applicator or the like can be used as known means.

In the first voltage application step, the first voltage ($V_1$) may be a voltage equal to or higher than the oxidation potential (E), e.g., a voltage satisfying $E \leq V_1$ (V), and the upper limit of the first voltage is not limited. When the oxidation potential is determined based on the potentials obtained by multiple measurements, preferably, the oxidation potential is the maximum potential of the potentials obtained by the multiple measurements. In some embodiments, the first voltage may be a voltage satisfying $E+0.15 \leq V_1$ (V) or $E+0.25 \leq V_1$ (V), because it reduces the noise at the time of acquiring the signal. In additional embodiments, the upper limit of the first voltage 1 may be the maximum value of the voltage with which hydrolysis of water in the reaction system is not caused, and also may be a voltage satisfying $V_1 \leq E+1.15$ (V), $V_1 \leq E+1.05$ (V), $V_1 \leq E+1$ (V), or $V_1 \leq E+0.95$ (V) because it reduces the influence of the interfering substance. In further embodiments, the first voltage may be a voltage satisfying $E \leq V_1 \leq E+1.15$ (V), $E+0.15 \leq V_1 \leq E+1.05$ (V), or $E+0.25 \leq V_1 \leq E+0.95$ (V) because it reduces the noise at the time of acquiring the signal and reduces the influence of the interfering substance. As a specific example, when the electron transfer substance is a ruthenium complex and the material for the electrode system is carbon, the first voltage is, for example, a voltage in the range from 50 to 1200 mV, from 200 to 1100 mV, or from 300 to 1000 mV. In yet further embodiments, the first voltage may be in the range from about 50, 60, 70, 80, 90, 100, 110, 120, 130, 140, 150, 160, 170, 180, 190, 200, 210, 220, 230, 240, 250, 260, 270, 280, 290 or 300 mV to about 900, 1000, 1100, 1200, 1300 or 1400 mV. The first voltage may be constant or changable, for example, and the former is better.

In the first voltage application step, the duration for applying the first voltage is not limited and is, for example, from 0.1 to 10 seconds, from 0.5 to 8 seconds, or from 1 to 5 seconds. In some embodiments, the duration for applying the first voltage is from about 0.1, 0.3, 0.5, 0.8, 1, 1.2, 1.5, 2, 3, 4 or 5 seconds to 5, 6, 7, 8, 9 or 10 seconds. The voltage may be continuously or not continuously applied to the electrode system, for example. In the first voltage application step, the current of the electrode system may be determined appropriately according to the reaction system, for example.

As described above, in the second voltage application step, the second voltage is applied to the electrode system. The second voltage application step can be performed by applying the second voltage to the electrode system that is in contact with the reaction system, for example. The second voltage may be applied to the electrode system using the voltage application unit, for example.

The second voltage application step may be performed sequentially or not sequentially from the first voltage application step, for example. In the former case, the second voltage application step is performed at the same time as the completion of the first voltage application step.

In the second voltage application step, the second voltage ($V_2$) may be a voltage lower than the oxidation potential (E), e.g. a voltage satisfying $V_2<E$ (V), and the lower limit of the second voltage is not limited. When the oxidation potential is determined based on the potentials obtained by multiple measurements, preferably, the oxidation potential is the minimum potential of the potentials obtained by the multiple measurements. The second voltage may be a potential close to the oxidation potential, for example, because the noise at the time of acquiring the signal is further reduced as the second voltage comes close to the oxidation potential. The lower limit of the second voltage may be a voltage satisfying $E-0.25 \leq V_2$ (V), $E-0.2 \leq V_2$ (V), $E-0.15 \leq V_2$ (V), or $E-0.1 \leq V_2$ (V), for example, because it reduces the influence of the interfering substance. The second voltage may be a voltage satisfying $E-0.25 \leq V_2 \leq E$ (V), $E-0.2 \leq V_2 \leq E$ (V), $E-0.15 \leq V_2 < E$ (V), or $E-0.1 \leq V_2 < E$ (V), for example, because it reduces the noise at the time of acquiring the signal and reduces the influence of the interfering substance. As a specific example, when the electron transfer substance is a ruthenium complex and the material for the electrode system is carbon, the second voltage is, for example, equal to or higher than −200 mV and lower than 50 mV, equal to or higher than −100 mV and lower than 50 mV, or equal to or higher than −50 mV and lower than 50 mV. In some embodiments, the second voltage is equal or higher than about −250, −200, −150, −100, −50 or −30 mV, and lower than 60, 50, 40, 30, 20, 10 mV. The second voltage may be constant or changable, for example, and the former is better.

In the second voltage application step, the duration for applying the second voltage is not limited and can be determined appropriately according to the time point of acquiring the signal in the signal acquisition step to be described below. The duration for applying the second voltage is, for example, from 0.001 to 10 seconds, from 0.001 to 2 seconds, from 0.005 to 1.5 seconds, or from 0.01 to 1 second. In some embodiments, the duration for applying the second voltage may be from about 0.001, 0.003, 0.005, 0.01, 0.015, 0.03, 0.05, 0.08 or 0.1 to about 0.5, 1, 1.5, 2, 3, 4, 5, 8, 10, or 12 seconds. The voltage may be continuously or not continuously applied to the electrode system, for example. In the second voltage application step, the current of the electrode system can be determined appropriately according to the reaction system, for example. In additional embodiments, the duration for applying the first voltage described herein may be longer than that for applying the second voltage.

As described above, in the signal acquisition step, a signal is acquired by the electrode system in the second voltage application step. The signal can be acquired using the signal acquisition unit (for example, the detector or the like) connected to the electrode system, for example. When the electrode system includes a plurality of working electrodes, the signals may be acquired by the plurality of working electrodes.

In the signal acquisition step, the number of acquisitions of signal is not limited and the acquisition can be, for example, a single acquisition or multiple acquisitions. In the former case, for example, the signal may be a signal acquired at a single time point or a signal continuously acquired within a given time. When the signal is continuously acquired, for example, the signal may be the integral value of the signal. In the latter case, for example, the signal may include signals acquired at a plurality of time points or signals acquired by the plurality of working electrodes.

The signals acquired at a plurality of time points mean the signals acquired at several time points over time, for example. The number of the time points (i.e. the number of acquisitions of signal) is more than one, two, three, four or five. For example, the number of the time points is two time points or more and may be 2, 3, 4, 5, 6, 7, 8, 9 or 10 time points In the signal acquisition step, the timing of acquiring the signal is not limited and can be determined appropriately according to the target component, the redox catalyst, the electron transfer substance, the first voltage, the second voltage and the like, for example. As a specific example, the signal may be a signal acquired within 0.4 seconds, 0.2 seconds, 0.1 seconds, or 0.05 seconds with reference to the time of the second voltage application as 0 second and the signal may be a signal acquired in the range from 0 to 0.4 seconds, from 0.05 to 0.4 seconds, from 0 to 0.2 seconds, from 0.05 to 0.2 seconds, from 0 to 0.1 seconds, from 0.05 to 0.1 seconds, or 0 to 0.05 seconds with reference to the time of the second voltage application because it reduces the influence of the interfering substance. When the signal is a signal acquired at a single time point, the timing of acquiring the signal is as follow. That is, the signal is, for example, a signal acquired within 0.2 seconds, 0.15 seconds, or 0.1 seconds with reference to the time of the second voltage application and may be a signal acquired in the range from 0 to 0.2 seconds, from 0.05 to 0.2 seconds, from 0 to 0.15 seconds, from 0.05 to 0.15 seconds, from 0 to 0.1 seconds, or from 0.05 to 0.1 seconds with reference to the time of the second voltage application. When the signal is the integral value of the signal, the timing of acquiring the signal is as follows. That is, the signal is, for example, a signal acquired in the range from 0 to 0.2 seconds, from 0.05 to 0.2 seconds, from 0 to 0.15 seconds, from 0.05 to 0.15 seconds, from 0 to 0.1 seconds, or from 0.05 to 0.1 seconds with reference to the second voltage application. When the signal includes signals acquired at a plurality of time points, the timing of acquiring the signal is as follows. That is, the signal which is acquired first out of the signals is, for example, a signal acquired within 0.5 seconds, 0.3 seconds, or 0.1 seconds and may be a signal acquired in the range from 0 to 0.2 seconds, from 0.05 to 0.2 seconds, from 0 to 0.15 seconds, from 0.05 to 0.15 seconds, from 0 to 0.1 seconds, or 0.05 to 0.1 seconds with reference to the time of the second voltage application. Furthermore, the signal which is acquired last out of the signals is, for example, a signal acquired within 0.5 seconds, 0.3 seconds, or 0.1 seconds and may be a signal acquired in the range from 0 to 0.2 seconds, from 0.05 to 0.2 seconds, from 0 to 0.15 seconds, from 0.05 to 0.15 seconds, from 0 to 0.1 seconds, or from 0.05 to 0.1 seconds with reference to the time of the second voltage application. As a specific example, when the target component is glucose, the redox catalyst is glucose dehydrogenase, and the electron transfer substance is a ruthenium complex, the timing of acquiring the signal is as follows. That is, the signal is, for example, a signal acquired in the range from 0 to 0.2 seconds, from 0.05 to 0.2 seconds, from 0 to 0.15 seconds, from 0.05 to 0.15 seconds, from 0 to 0.1 seconds, or from 0.05 to 0.1 seconds with reference to the time of the second voltage application.

When the signal includes signals acquired at a plurality of time points, the interval between the times of acquiring the signals is not limited, and can be determined appropriately according to the type of the signal, the target component, the first voltage, the second voltage, and the like, for example.

As a specific example, the signals are signals acquired at intervals of, for example, 0.01 to 10 seconds, 0.05 to 5 seconds, 0.1 to 3 seconds.

The measurement method according to the present invention may include the following step: calculating an amount of a target component in the sample from the signal. In the calculation step, for example, the amount of the target component can be calculated based on the obtained signal and the correlation between the signal and the amount of the target component in a sample. The correlation can be represented, for example, by a calibration curve, a regression line, a calibration table, or the like. The correlation can be obtained, for example, by plotting the signal obtained by the measurement method of the present invention and the amount of the target component in the standard sample whose target component amount is known. The standard sample may be a dilution series of the target components. The calculation in this manner allows a quantity analysis with high reliability. The calculation step may be performed by a calculation unit such as data processing equipment or the like which is hardware, for example. Specifically, the calculation step can be performed by the above described biosensor. The data processing equipment may be provided with a CPU, or the like, for example.

In the measurement method according to the present invention, for example, the signal may be corrected by a correction signal because it reduces the influence of the interfering substance and allows a measurement with high reliability. In some embodiments, the measurement method according to the present invention includes the following steps: acquiring a correction signal by the electrode system; and correcting the signal based on the correction signal, wherein in the calculation step, the amount of the target component in the sample is calculated from a corrected signal.

The correction signal is a signal that corrects the influence of the interfering substance, for example. Examples of the interfering substance include hematocrit, ascorbic acid, sugar, and a blood coagulation inhibitor such as ethylenediaminetetraacetate (EDTA). Specifically, examples of the correction signal include an interfering substance-derived signal acquired by the electrode system and a target component-derived signal acquired by the electrode system, more specifically, a target component-derived signal acquired by a signal acquisition unit connected to the electrode system.

When the correction signal is an interfering substance-derived signal, the electrode group used in the measurement of the correction signal may be the same electrode group as or a different electrode group from the one used in the measurement of the target component, for example. In the latter case, for example, the electrode system includes an electrode group for measuring the interfering substance in addition to an electrode group for measuring the target component. Furthermore, for example, the reaction system may include a reagent or the like that is required for acquiring the interfering substance-derived signal in accordance with the type of the interfering substance. The method for acquiring a correction signal by the electrode system is not limited to a particular method, and, for example, can be performed by a known method in accordance with the type of the interfering substance. The method of correcting the signal by the interfering substance-derived signal is not limited to a particular method, and the method may be, for example, a method of correcting the signal based on the correlation between the interfering substance-derived signal and the change of the signal. The correlation can be obtained using the standard sample whose target component amount is known and that includes different interfering substances by plotting the signal obtained by the measurement method of the present invention and the amount of the target component in the standard sample, for example.

When the correction signal is the target component-derived signal, the correction signal may include a plurality of signals acquired in the signal acquisition step, for example. With reference to the plurality of signals, for example, the above description as to the signals can be referred to. The method of correcting a signal by the correction signals is not limited to a particular method and the method can be, for example, a method of correcting a signal based on the relationship between the amount of the target component and the signals corresponding thereto. With reference to the method of correcting a signal, the specification of U.S. Pat. No. 8,760,178 can be referred to as providing a specific example. The correction step can be performed by a correction unit such as the data processing equipment or the like which is hardware, for example. Specifically, the correction step can be performed by the above described biosensor.

The amount of the target component can be calculated based on the corrected signal and the correlation between the signal and the amount of the target component in a sample.

<Apparatus for Measuring a Target Component>

As described above, the apparatus for measuring a target component according to the present invention is an apparatus for measuring a target component, including: an electrode system; a voltage application unit that applies a first voltage ($V_1$) and a second voltage ($V_2$) to the electrode system in the presence of a sample, a redox catalyst to a target component, and an electron transfer substance; and a signal acquisition unit that acquires a signal by the electrode system in the second voltage ($V_2$) application, wherein the first voltage is a voltage equal to or higher than the oxidation potential (E) of the electron transfer substance, the second voltage is a voltage lower than the oxidation potential (E) of the electron transfer substance, and the apparatus is used in the method for measuring a target component according to the present invention.

The measurement apparatus according to the present invention is characterized in that the first voltage applied by the voltage application unit is a voltage equal to or higher than the oxidation potential (E) of the electron transfer substance and the second voltage is a voltage lower than the oxidation potential (E) of the electron transfer substance and that it is used in the method for measuring a target component according to the present invention, and other configurations and combinations are not limited. According to the measurement apparatus of the present invention, for example, the measurement method of the present invention can be performed easily. With reference to the measurement apparatus according to the present invention, for example, the above description as to the measurement method of the present invention can be referred to.

The examples of the present invention are described below. The present invention, however, is by no means limited by the following examples.

EXAMPLE

Example 1

The oxidation potential was measured using a biosensor provided with the redox catalyst, the electron transfer substance, and the electrode system, and it was examined that a target component can be measured by the measurement method of the present invention.

(1) Biosensor Production

Figure 1:
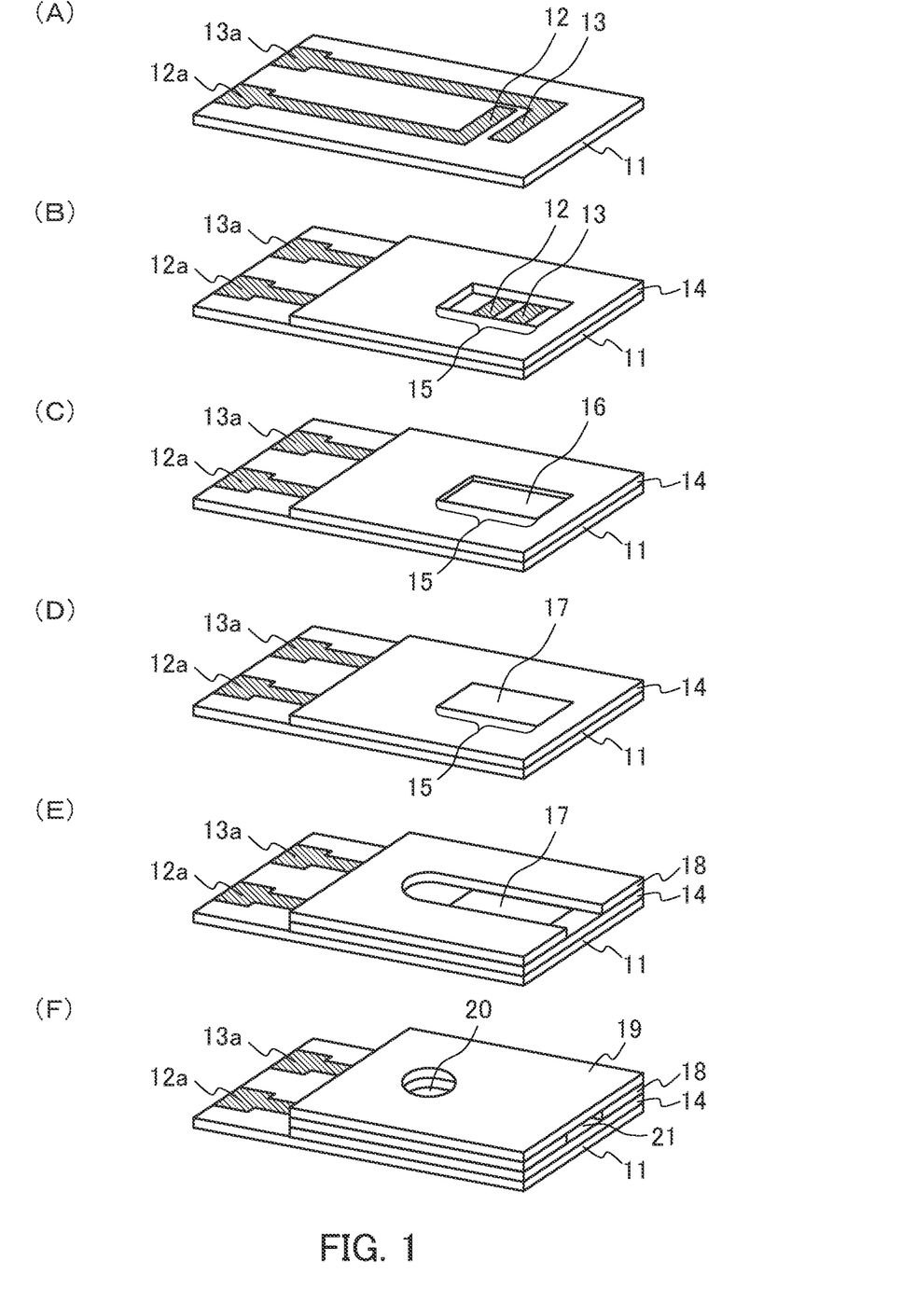
FIG. 1 depicts perspective views showing a method of producing a biosensor used in Example 1 of the present invention.

The biosensor was produced by the following procedures as shown in (A) to (F) of FIG. 1. First, as shown in (A) of FIG. 1, as a glucose sensor insulating substrate 11, a PET (polyethylene terephthalate) substrate (length: 50 mm, width: 6 mm, thickness 250 μm) was prepared, and a carbon electrode system having a working electrode 12 and a counter electrode 13 each provided with a lead section was formed on one surface of the substrate by screen printing.

Subsequently, as shown in (B) of FIG. 1, an insulating layer 14 was formed on the electrode. First, insulating resin polyester was dissolved in a solvent carbitol acetate so as to achieve a concentration of 75% (wt) to prepare insulating paste, and this was applied to the electrode by screen printing. Printing conditions were as follows: 300 mesh screen, squeegee pressure: 40 kg, and printing amount: 0.002 mL per electrode area 1 $cm^2$. On this occasion, the screen printing was not performed on the detection section 15 and lead sections 12a and 13a. This was heated at 155° C. for 20 minutes to form the insulating layer 14.

Subsequently, as shown in (C) of FIG. 1, an inorganic gel layer 16 was formed on a detection section 15 on which the insulating layer 14 was not formed. First, an inorganic gel-forming liquid (pH7.5) containing 0.3% (wt) synthetic smectite (product name: "Lucentite SWF", produced by CO-OP CHEMICAL Co. Ltd.), 6.0% (wt) ruthenium compound ([$Ru(NH_3)_6$]$Cl_3$, produced by Dojindo Laboratories), sodium acetate, and succinic acid was prepared. 1.0 μL of inorganic gel-forming liquid was dispensed to the detection section 15. On this occasion, the surface area of the detection section 15 was about 0.6 $cm^2$ and the surface area of each of the electrodes 12 and 13 on the detection section 15 was 0.12 $cm^2$. This was dried at 30° C. to form the inorganic gel layer 16.

Subsequently, as shown in (D) of FIG. 1, an enzyme layer 17 was formed on the inorganic gel layer 16. First, an enzyme liquid containing 2.7 U *Aspergillus oryzae* type FAD-GDH (product name: "Glucosedehydrogenase (FAD-dependent) (GLD-351)", produced by Toyobo Co., Ltd.), 25% (wt) 1-methoxy PMS (produced by Dojindo Laboratories), and an ACES buffer solution (pH7.5) was prepared. 1.0 μL of the enzyme liquid was dispensed to the inorganic gel layer 16 of the detection section 15, and this was dried at 30° C. to form the enzyme layer 17.

As shown in (E) of FIG. 1, a spacer 18 including an opening was disposed on the insulating layer 14. Then, as shown in (F) of FIG. 1, a cover 19 including a through-hole 20 serving as an air hole was disposed on the spacer 18 to produce a biosensor. The space of the opening of the spacer 18 sandwiched between the cover 19 and the insulating layer 14 has a capillary structure, and the space was used as a sample supply section 21.

(2) Oxidation Potential Measurement

Whole blood (Ht value: 42%) was introduced into the biosensor, and a current value was measured under the above-described measurement conditions of the oxidation potential. The current value was measured three times using a self-prepared electrochemical measuring instrument.

Figure 2:
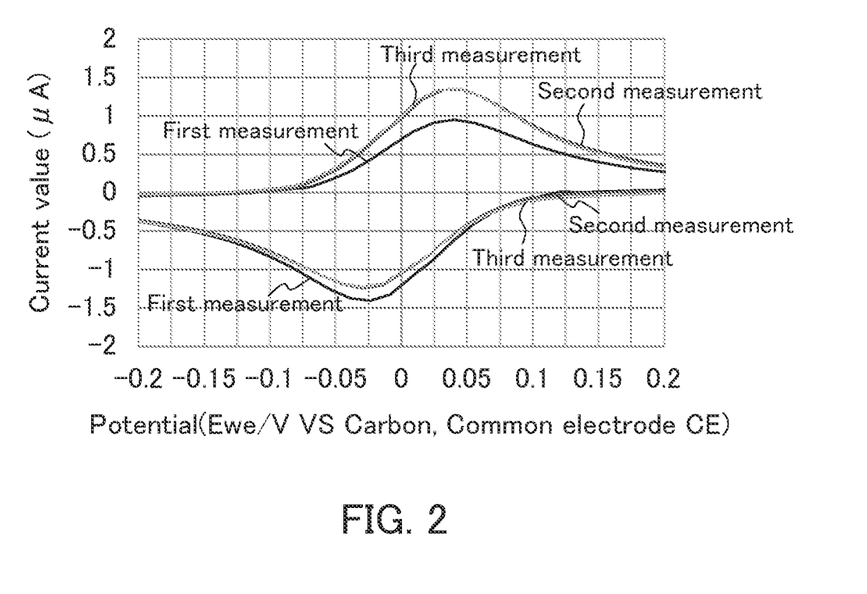
FIG. 2 is a cyclic voltammogram result showing the current value under the oxidation potential measurement conditions of Example 1 of the present invention.
Figure 3A:
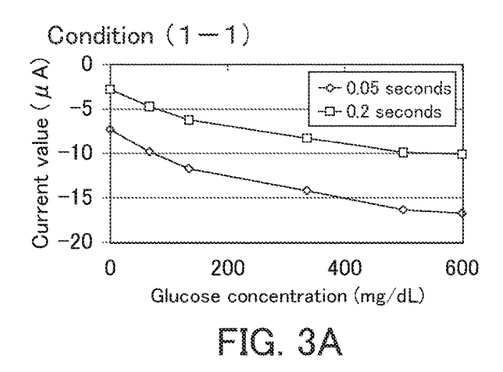
FIGS. 3A to 3F are graphs each showing the current values obtained in the glucose sample in Example 1 of the present invention.
Figure 3B:
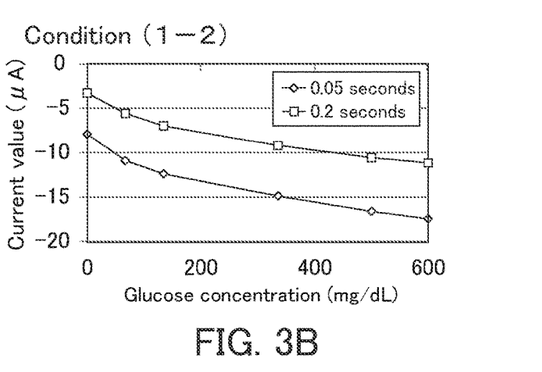
Figure 3C:
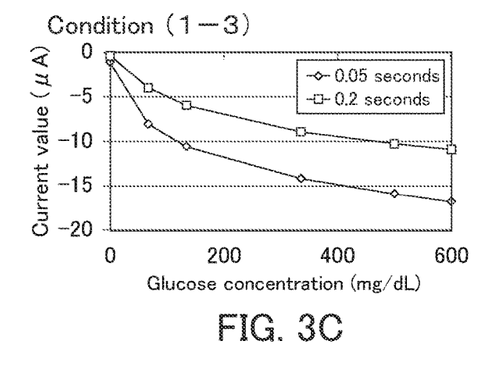
Figure 3D:
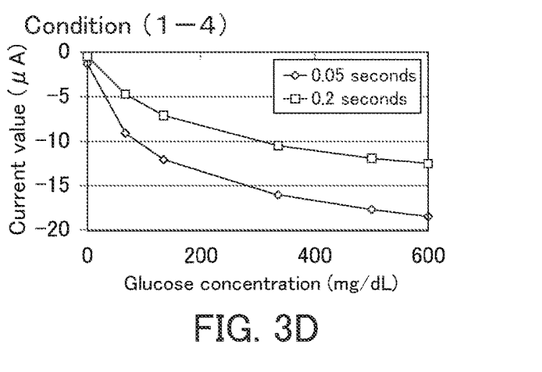
Figure 3E:
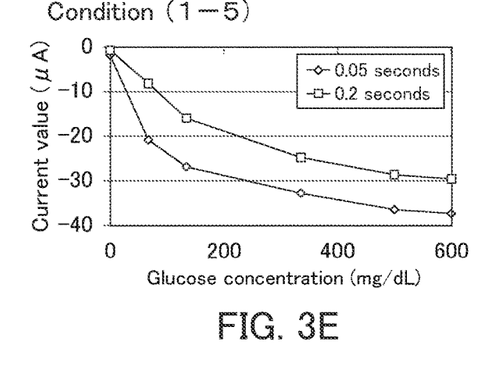
Figure 3F:
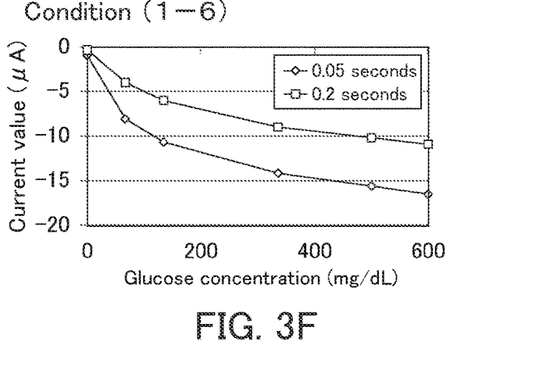

The results are shown in FIG. 2. FIG. 2 is a cyclic voltammogram showing a current value under the measurement conditions of the oxidation potential. Note that FIG. 2 shows the current value in the potential range from −0.2 to 0.2 V. In FIG. 2, the horizontal axis indicates the potential applied to the electrode system and the vertical axis indicates the response current value. As shown in FIG. 2, the peaks were seen between 30 to 50 mV (positive current value). This shows that the oxidation potential of the electron transfer substance in the biosensor was from 30 to 50 mV.

(3) Target Component Measurement 1

Next 42% hematocrit (Ht) glucose sample 1 containing glucose having a predetermined concentration (0, 67, 134, 336, or 600 mg/dL) was prepared.

As to each glucose sample, using the biosensor and the electrochemical measuring instrument, the first voltage and the second voltage were applied under the following voltage application conditions (1-1) to (1-6) as the conditions of Example 1 and the current value at 0.05 or 0.2 seconds was measured with reference to the time of the second voltage application.

(Voltage Application Conditions)
(1-1) first voltage application: 1 V, 1 second
second voltage application: 0 V, 5 seconds
(1-2) first voltage application: 1 V, 2 seconds
second voltage application: 0 V, 5 seconds
(1-3) first voltage application: 350 mV, 2 seconds
second voltage application: 0 V, 5 seconds
(1-4) first voltage application: 350 mV, 2 seconds
second voltage application: 10 mV, 5 seconds
(1-5) first voltage application: 350 mV, 2 seconds
second voltage application: −100 mV, 5 seconds
(1-6) first voltage application: 200 mV, 2 seconds
second voltage application: 0 V, 5 seconds The results are shown in FIGS. 3A to 3F. FIGS. 3A to 3F are graphs each showing the current values obtained in the glucose sample. FIGS. 3A to 3F show the results of the conditions (1-1) to (1-6), respectively. In each of FIGS. 3A to 3F, the horizontal axis indicates the glucose concentration and the vertical axis indicates the current value, diamonds each show the result at 0.05 seconds, and squares each show the result at 0.2 seconds. As shown in FIGS. 3A to 3F, under any voltage condition and signal acquisition time, the glucose concentration in the glucose sample and the current value show a negative correlation. Since the glucose concentration and the current value show a negative correlation, the glucose concentration in the sample can be calculated by the current value obtained from the sample. This shows that a target component including glucose can be measured by the measurement method of the present invention.

(4) Target Component Measurement 2

42% hematocrit (Ht) glucose sample 2 containing glucose having a predetermined concentration (0, 67, 336, or 600 mg/dL) was prepared. Then, as to each glucose sample, the current value at 0.05, 0.2, or 0.4 seconds was measured in the same manner as the item (3) of Example 1 except that the following voltage application conditions (2-1) to (2-3) were selected as the conditions of Example 2 instead of the conditions (1-1) to (1-6).

Figure 4A:
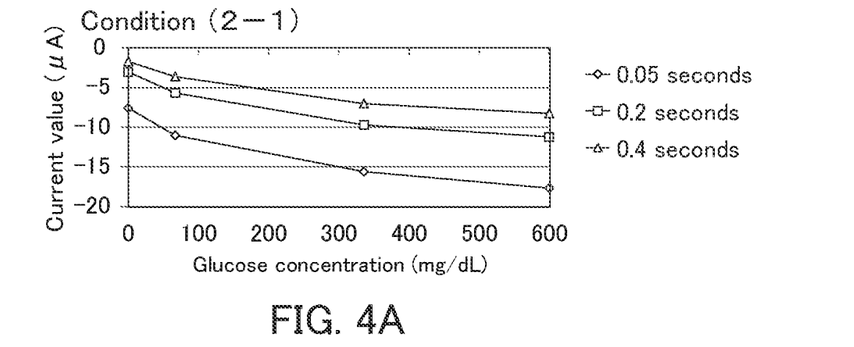
FIGS. 4A to 4C are graphs each showing the current values obtained in the glucose sample in Example 1 of the present invention.
Figure 4B:
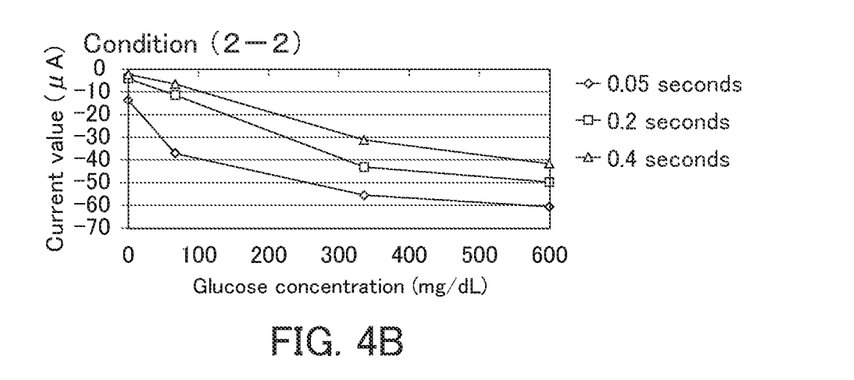
Figure 4C:
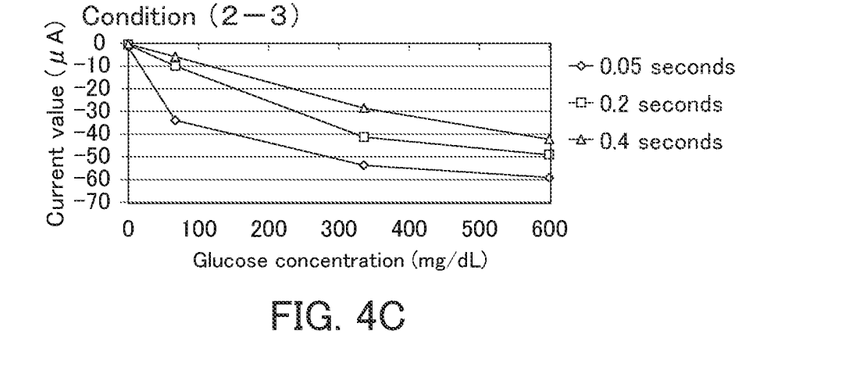

(Voltage Application Conditions)
(2-1) first voltage application: 1 V, 2 seconds
second voltage application: 0 V, 5 seconds
(2-2) first voltage application: 1 V, 2 seconds
second voltage application: −200 mV, 5 seconds
(2-3) first voltage application: 350 mV, 2 seconds
second voltage application: −200 mV, 5 seconds The results are shown in FIGS. 4A to 4C. FIGS. 4A to 4C are graphs each showing the current values obtained in the glucose sample. FIGS. 4A to 4C show the results of the conditions (2-1) to (2-3), respectively. In each of FIGS. 4A to 4C, the horizontal axis indicates the glucose concentration and the vertical axis indicates the current value, diamonds each show the result at 0.05 seconds, squares each show the result at 0.2 seconds, and triangles each show the result at 0.4 seconds. As shown in FIGS. 4A to 4C, under any voltage condition and signal acquisition time, the glucose concentration in the glucose sample and the current value show a negative correlation. Because the glucose concentration and the current value show a negative correlation, it can be said that the glucose concentration in the sample can be calculated by the current value obtained from the sample. This shows that a target component including glucose can be measured by the measurement method of the present invention.

Example 2

It was examined that the influence of hematocrit in the measurement of a target component is reduced by the measurement method of the present invention.

A glucose sample 3 having a predetermined Ht value (0, 20, 42, or 70%) containing 336 or 600 mg/dL glucose was prepared. Then, the current value at 0.2 seconds was measured with reference to the time of the second voltage application in the same manner as the item (3) of Example 1 under the condition (1-2) except that the glucose sample 3 was used instead of the glucose sample 1. Then, on the basis of the following expression (1), the degree of influence of the Ht value with reference to the current value of the glucose sample 3 having 42% Ht value was calculated. As a control, the degree of influence of the Ht value was calculated in the same manner except that 200 mV voltage instead of the first voltage and the second voltage was applied to the biosensor for 5 seconds as the condition of the comparative example, and the current value at 5 seconds was measured with reference to the time of starting the voltage application.

$$E_h = (S_g/B_g) \times 100 - 100 \quad (1)$$

Figure 5A:
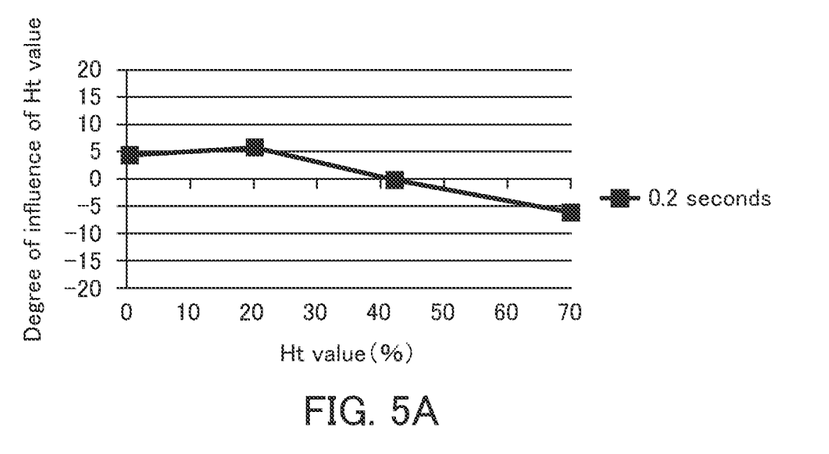
FIGS. 5A to 5C are graphs each showing the degree of influence of the Ht value in Example 2 of the present invention.
Figure 5B:
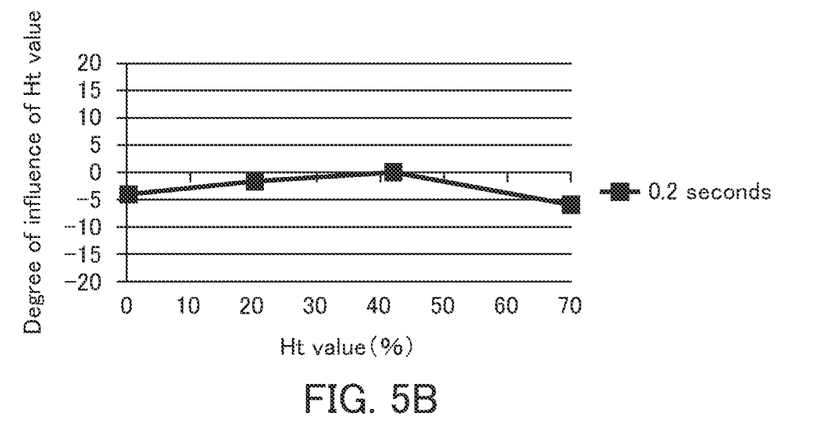
Figure 5C:
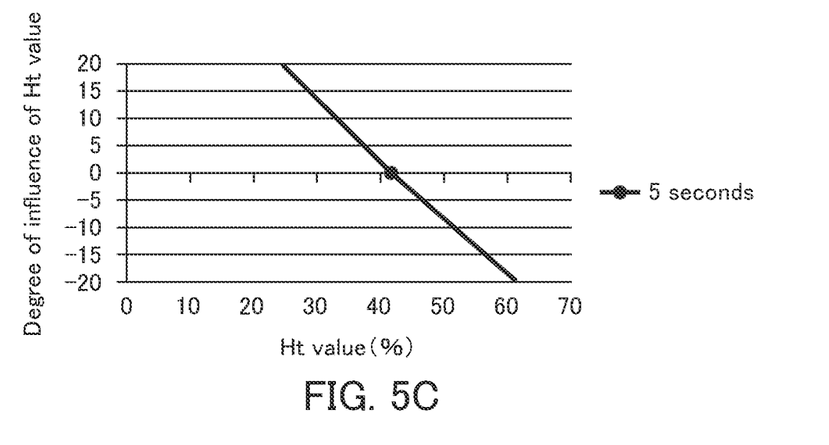

$E_h$: degree of influence of Ht value
$S_g$: current value of glucose sample
$B_g$: current value of glucose sample having 42% Ht value The results are shown in FIGS. 5A to 5C. FIGS. 5A to 5C are graphs each showing the degree of influence of the Ht value. FIG. 5A shows the result of the glucose sample containing 336 mg/dL glucose of the present example, FIG. 5B shows the result of the glucose sample containing 600 mg/dL glucose of the present example, and FIG. 5C shows the result of the control. Furthermore, in each of FIGS. 5A to 5C, the horizontal axis indicates the Ht value and the vertical axis indicates the degree of influence of the Ht value. As shown in FIG. 5C, when a constant voltage was applied, the degree of influence of the Ht value to the obtained current value was increased as the Ht value departed from 42%. In contrast, as shown in FIGS. 5A and 5B, when the first voltage equal to or higher than the oxidation potential and the second voltage lower than the oxidation potential were applied, the degree of influence of the Ht value to the obtained current value was low with any Ht value. This shows that the influence of hematocrit is reduced by the measurement method of the present invention.

Example 3

It was examined that the influence of hematocrit in the measurement of a target component is reduced in cases where various first voltages and second voltages which respectively satisfy the conditions of the first voltage and second voltage of the measurement method of the present invention are applied.

The current value at 0.05 or 0.2 seconds was measured with reference to the time of the second voltage application in the same manner as the item (3) of Example 1 except that the glucose sample 3 containing 336 mg/dL glucose was used and the first voltage and the second voltage were applied under the following conditions (3-1) to (3-11) as the conditions of the present example. Then, with reference to each measurement time, the degree of influence of the Ht value was calculated in the same manner as Example 2. As a control, the degree of influence of the Ht value was calculated in the same manner except that the voltage was applied under the following conditions (3-12) to (3-14) as the conditions of the comparative example. The current value at 0.4 seconds was measured under the conditions (3-4), (3-5), (3-13), and (3-14) with reference to the time of the second voltage application, and the degree of influence of the Ht value was calculated in the same manner.

Figure 6A:
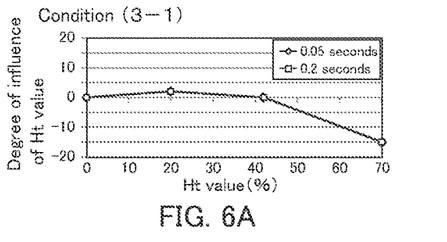
FIGS. 6A to 6K are graphs each showing the degree of influence of the Ht value in Example 3 of the present invention.
Figure 6B:
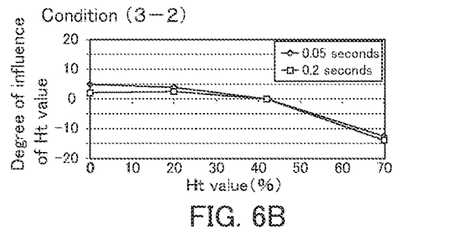
Figure 6C:
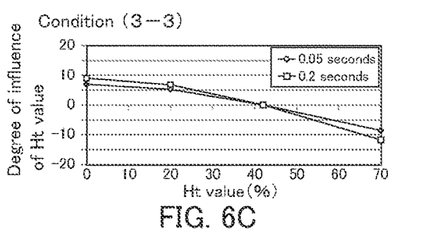
Figure 6D:
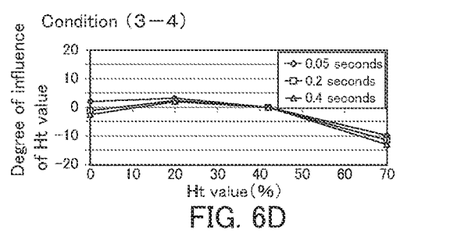
Figure 6E:
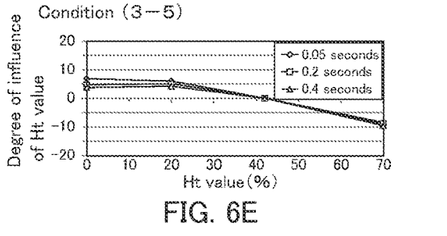
Figure 6F:
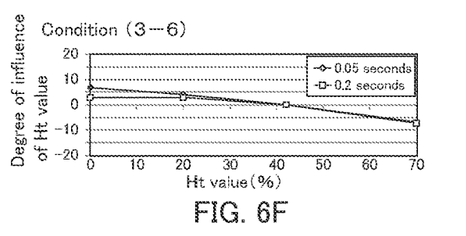
Figure 6G:
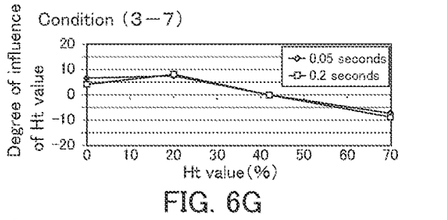
Figure 6H:
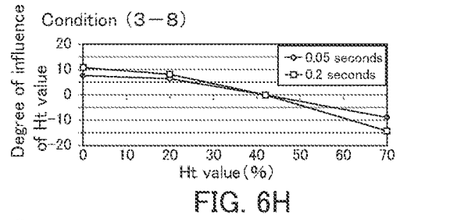
Figure 6I:
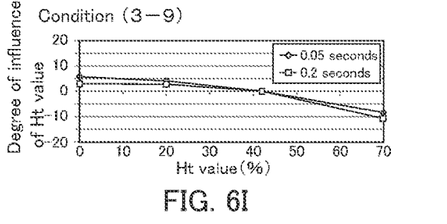
Figure 6J:
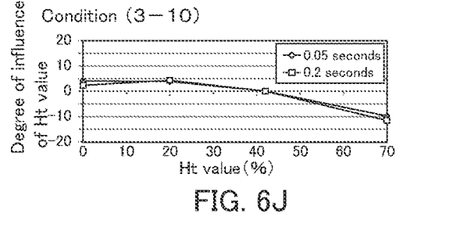
Figure 6K:
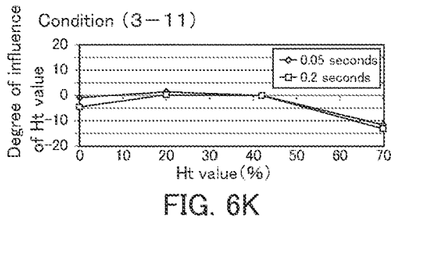
Figure 7A:
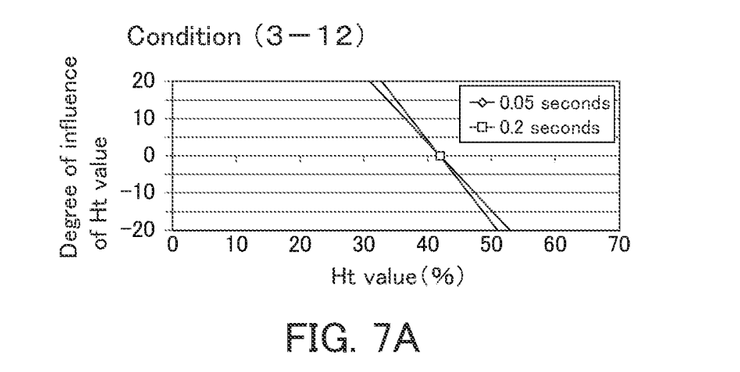
FIGS. 7A to 7C are graphs each showing the degree of influence of the Ht value in Example 3 of the present invention.
Figure 7B:
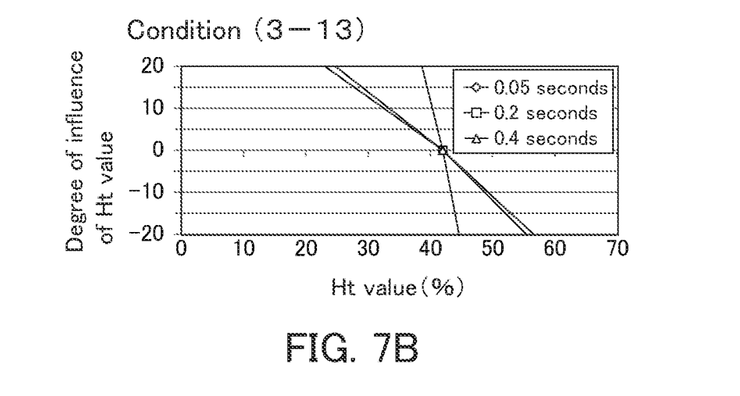
Figure 7C:
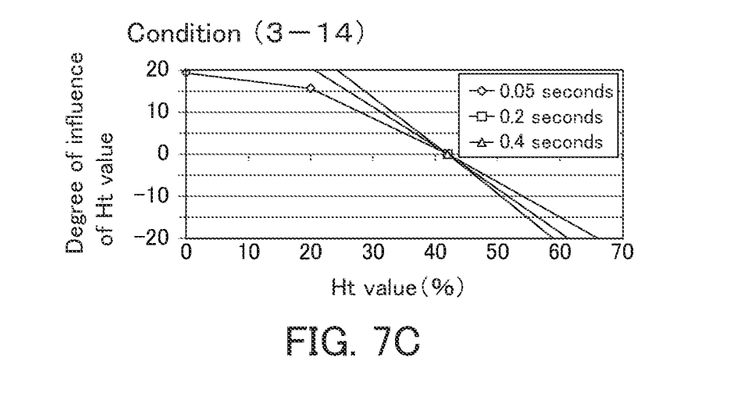

(Voltage Application Condition)
(3-1) first voltage application: 1 V, 2 seconds
second voltage application: 0 V, 2 seconds
(3-2) first voltage application: 500 mV, 2 seconds
second voltage application: 0V, 2 seconds
(3-3) first voltage application: 1 V, 5 seconds
second voltage application: 0 V, 2 seconds
(3-4) first voltage application: 1 V, 2 seconds
second voltage application: 0 V, 7 seconds
(3-5) first voltage application: 1 V, 2 seconds
second voltage application: 10 mV, 7 seconds
(3-6) first voltage application: 1 V, 1 second
second voltage application: 0 V, 5 seconds
(3-7) first voltage application: 1 V, 2 seconds
second voltage application: 0 V, 5 seconds
(3-8) first voltage application: 350 mV, 2 seconds
second voltage application: −100 mV, 5 seconds
(3-9) first voltage application: 350 mV, 2 seconds
second voltage application: 0 V, 5 seconds
(3-10) first voltage application: 350 mV, 2 seconds
second voltage application: 10 mV, 5 seconds
(3-11) first voltage application: 200 mV, 2 seconds
second voltage application: 0 V, 5 seconds
(3-12) first voltage application: 1 V, 2 seconds
second voltage application: 200 mV, 7 seconds
(3-13) first voltage application: 1 V, 2 seconds
second voltage application: 100 mV, 7 seconds
(3-14) first voltage application: −200 mV, 2 seconds
second voltage application: 0 V, 7 seconds The results are shown in FIGS. 6A to 6K and FIGS. 7A to 7C. FIGS. 6A to 6K and FIGS. 7A to 7C are graphs each showing the degree of influence of the Ht value. FIGS. 6A to 6K show the results of the conditions (3-1) to (3-11), respectively. FIGS. 7A to 7C show the results of the conditions (3-12) to (3-14), respectively. In each of FIGS. 6A to 6K and FIGS. 7A to 7C, the horizontal axis indicates the Ht value and the vertical axis indicates the degree of influence of the Ht value, diamonds each show the result at 0.05 seconds, squares each show the result at 0.2 seconds, and triangles each show the result at 0.4 seconds. As shown in FIGS. 6A to 6K, in the cases of the the conditions (3-1) to (3-11) in each of which the first voltage equal to or higher than the oxidation potential and the second voltage lower than the oxidation potential were applied, the degree of influence of the Ht value to the obtained current value was low with any Ht value and any measurement time. In contrast, as shown in FIGS. 7A to 7C, in the cases of the conditions (3-12) and (3-13) in each of which the first voltage and the second voltage equal to or higher than the oxidation potential were applied and the case of the condition (3-14) in which the first voltage and the second voltage lower then the oxidation potential are applied, the degree of influence of the Ht value to the obtained current value was increased (i.e. the influence of the Ht value was great) as the Ht value departed from 42%. As shown in FIGS. 6I and 6K, when the first voltage was a voltage close to the oxidation potential of the electron transfer substance, the influence of hematocrit could further be reduced. As shown in FIGS. 6H to 6J, when the second voltage was a voltage close to the oxidation potential of the electron transfer substance, the influence of hematocrit could further be reduced. As described above, it was found that the influence of hematocrit in the measurement of a target component can be reduced even in cases where various first voltages and second voltages which respectively satisfy the conditions of the first voltage and second voltage of the measurement method of the present invention are applied and that the influence of hematocrit can further be reduced when the first voltage and the second voltage are voltages close to the oxidation potential of the electron transfer substance.

Example 4

It was examined that the influence of ascorbic acid in the measurement of a target component is reduced by the measurement method of the present invention.

A blood sample containing 336 mg/dL glucose and 0 or 6 mg/dL ascorbic acid was prepared using the venous blood which has been collected the day before the measurement day. The oxygen partial pressure of the blood sample was from 30 to 70 mmHg.

The current value was measured in the same manner as the item (3) of Example 1 under the condition (1-2) except that the current value at 0.05 or 0.2 seconds was measured with reference to the time of the second voltage application using the blood sample instead of the glucose sample 1. The current value was measured using 10 samples for each blood sample. Then, on the basis of the expression (2), the degree of influence of ascorbic acid with reference to the current value of the blood sample containing 0 mg/dL ascorbic acid was calculated. Furthermore, on the basis of the current values calculated from the 10 samples, the coefficient of variation (CV value) was calculated. As a control, the degree of influence of ascorbic acid and the CV value were calculated in the same manner except that 200 mV voltage instead of the first voltage and the second voltage was applied to the biosensor for 20 seconds, and the current value at 5 seconds was measured with reference to the time of starting the voltage application.

$$E_a = (S_a/B_a) \times 100 - 100 \qquad (2)$$

Figure 8A:
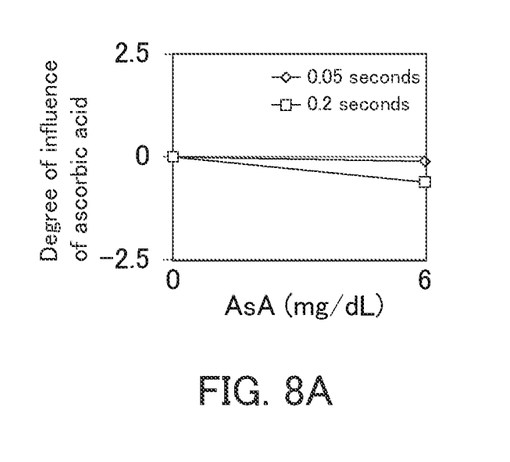
FIGS. 8A and 8B are graphs each showing the degree of influence of ascorbic acid in Example 4 of the present invention.
Figure 8B:
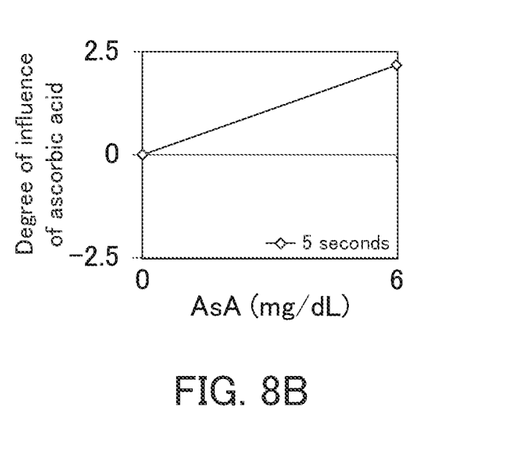

$E_a$: degree of influence of ascorbic acid
$S_a$: current value of blood sample
$B_a$: current value of blood sample having 0 mg/dL ascorbic acid The results of the degree of influence of ascorbic acid are shown in FIGS. 8A and 8B. FIGS. 8A and 8B are graphs each showing the degree of influence of ascorbic acid. FIG. 8A shows the result of the present example and FIG. 8B shows the result of the control. In each of FIGS. 8A and 8B, the horizontal axis indicates the ascorbic acid concentration (AsA(mg/dL)) and the vertical axis indicates the degree of influence of ascorbic acid. As shown in FIG. 8A, when the first voltage equal to or higher than the oxidation potential and the second voltage lower than the oxidation potential were applied, the degree of influence of ascorbic acid to the obtained current value was low regardless of the presence or absence of ascorbic acid. In contrast, as shown in FIG. 8B, when a constant voltage was applied in the case where the sample contains ascorbic acid, the degree of influence of ascorbic acid to the obtained current value was increased.

Figure 9A:
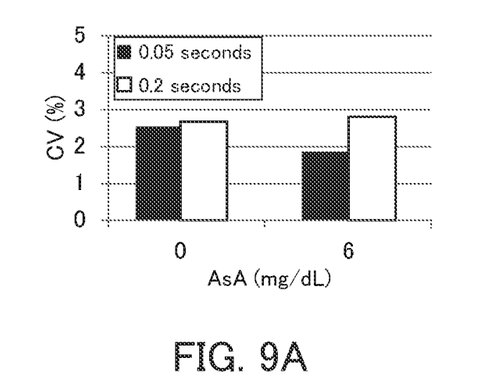
FIGS. 9A and 9B are graphs each showing the CV value in Example 4 of the present invention.
Figure 9B:
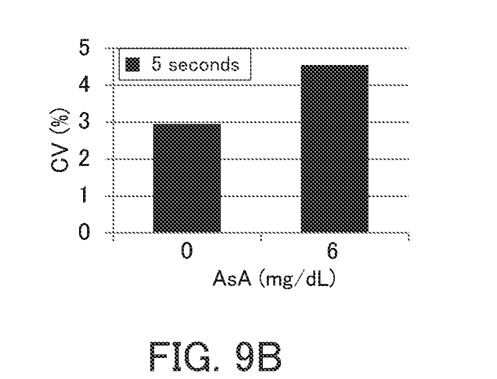

The results of the CV value are shown in FIGS. 9A and 9B. FIGS. 9A and 9B are graphs each showing the CV value. FIG. 9A shows the result of the present example and FIG. 9B shows the result of the control. In each of FIGS. 9A and 9B, the horizontal axis indicates the ascorbic acid concentration and the vertical axis indicates the CV value (CV (%)). As shown in FIG. 9A, when the first voltage equal to or higher than the oxidation potential and the second voltage lower than the oxidation potential were applied, the CV value of the obtained current value was constant regardless of the presence or absence of ascorbic acid. In contrast, as shown in FIG. 9B, when a constant voltage was applied in the case where the sample contains ascorbic acid, the CV value of the obtained current value was increased.

From the above description, it was found that the influence of ascorbic acid can be reduced by the measurement method of the present invention. It was also found that a target component can be measured with high reproducibility by the measurement method of the present invention.

While the present invention has been described above with reference to embodiments and examples, the present invention is by no means limited thereto. Various changes and modifications that may become apparent to those skilled in the art may be made in the configuration and specifics of the present invention without departing from the scope of the present invention.

This application claims priority from Japanese Patent Application No. 2015-238533 filed on Dec. 7, 2015 and Japanese Patent Application No. 2016-231201 filed on Nov. 29, 2016. The entire subject matter of the Japanese Patent Applications as well as all documents referred to herein are incorporated herein by reference in their entireties.

INDUSTRIAL APPLICABILITY

Target components including glucose can be measured according to the present invention. Thus, the present invention is very effective in analytic fields, clinical fields, and the like.

What is claimed is:

1. A method of measuring a concentration of glucose, comprising:
applying a first voltage ($V_1$) to an electrode system in the presence of a sample, a redox catalyst for glucose, and an electron transfer substance,
wherein the electrode system comprises a set of electrode group including a working electrode and a counter electrode, and the electron transfer substance donates an electron to the working electrode during the first voltage ($V_1$) application step;
applying a second voltage ($V_2$) to the electrode system, wherein the electron transfer substance accepts an electron from the working electrode during the second voltage ($V_2$) application step;
acquiring a signal, during the second voltage ($V_2$) application step, from the working electrode to which the electron transfer substance donates the electron during the first voltage ($V_1$) application step; and calculating an amount of glucose in the sample from the signal thereby obtaining the concentration of glucose in the sample from the signal, wherein the first voltage ($V_1$) is equal to or higher than an oxidation potential (E) of the electron transfer substance, and the second voltage ($V_2$) is lower than the oxidation potential (E) of the electron transfer substance.

2. The method according to claim 1, wherein the first voltage ($V_1$) satisfies $E \leq V_1 \leq E+1.15$ V.

3. The method according to claim 1, wherein the second voltage ($V_2$) satisfies $E-0.25$ V$\leq V_2 <$E.

4. The method according to claim 2, wherein the second voltage ($V_2$) satisfies $E-0.25$ V$\leq V_2 <$E.

5. The method according to claim 1, wherein the signal is acquired within 0.4 seconds with reference to a time of the second voltage application.

6. The method according to claim 5, wherein the first voltage ($V_1$) satisfies $E \leq V_1 \leq E+1.15$ V.

7. The method according to claim 5, wherein the second voltage ($V_2$) satisfies $E-0.25$ V$\leq V_2 <$E.

8. The method according to claim 5, wherein the first voltage ($V_1$) satisfies $E \leq V_1 \leq E+1.15$ V, and the second voltage ($V_2$) satisfies $E-0.25$ V$\leq V_2 <$E.

9. The method according to claim 1, wherein the signal is acquired at a single time point.

10. The method according to claim 1, wherein the signal is continuously acquired.

11. The method according to claim 1, wherein the signal includes signals acquired at a plurality of time points.

12. The method according to claim 1, wherein the redox catalyst is oxidoreductase or dehydrogenase.

13. The method according to claim 1, wherein the sample is a biological sample.

14. The method according to claim 1, comprising:
acquiring a correction signal by the electrode system; and
correcting the signal based on the correction signal, wherein
in the calculation step, the amount of glucose in the sample is calculated from a corrected signal.

15. The method according to claim 1, wherein the first voltage is higher than an oxidation potential (E) of the electron transfer substance.

16. An apparatus for measuring glucose, comprising:
an electrode system;
a voltage application unit that applies a first voltage ($V_1$) and a second voltage ($V_2$) to the electrode system in the presence of a sample, a redox catalyst to glucose, and an electron transfer substance,
wherein the electrode system comprises a set of electrode group including a working electrode and a counter electrode, and the electron transfer substance donates an electron to the working electrode during the first voltage ($V_1$) application step;
a signal acquisition unit that acquires a signal, during the second voltage ($V_2$) application step, by the working electrode to which the electron transfer substance donates the electron during the first voltage ($V_1$) application step, wherein the electron transfer substance accepts an electron from the working electrode during the second voltage ($V_2$) application step, and
a calculation unit that calculates an amount of glucose in the sample from the signal,
wherein
the first voltage ($V_1$) is a voltage equal to or higher than an oxidation potential (E) of the electron transfer substance,
the second voltage ($V_2$) is a voltage lower than the oxidation potential (E) of the electron transfer substance, and
the apparatus is used in the method for measuring glucose according to claim 1.

* * * * *